(12) United States Patent
Paradis et al.

(10) Patent No.: US 9,310,308 B2
(45) Date of Patent: Apr. 12, 2016

(54) MICRO-PLASMA EMISSION DETECTOR UNIT AND METHOD

(71) Applicant: LDETEK INC., Thetford Mines (CA)

(72) Inventors: Louis Paradis, Thetford Mines (CA); Dany Gagne, Thetford Mines (CA)

(73) Assignee: LDETEK INC., Thetford Mines, Quebec (CA)

( * ) Notice: Subject to any disclaimer, the term of this patent is extended or adjusted under 35 U.S.C. 154(b) by 418 days.

(21) Appl. No.: 13/931,207

(22) Filed: Jun. 28, 2013

(65) Prior Publication Data

US 2014/0160477 A1 Jun. 12, 2014

Related U.S. Application Data

(60) Provisional application No. 61/734,528, filed on Dec. 7, 2012.

(51) Int. Cl.
*G01N 21/66* (2006.01)
*G01N 21/68* (2006.01)

(52) U.S. Cl.
CPC ...................................... *G01N 21/68* (2013.01)

(58) Field of Classification Search
CPC ...................................................... G01N 21/66
See application file for complete search history.

(56) References Cited

U.S. PATENT DOCUMENTS

| | | | |
|---|---|---|---|
| 2,943,223 A | 6/1960 | Fay | |
| 3,032,654 A | 5/1962 | Fay et al. | |
| 3,549,326 A | 12/1970 | Dahlquist et al. | |
| 4,167,334 A | 9/1979 | Phillips | |
| 4,740,695 A | 4/1988 | Simpson | |
| 4,806,315 A | 2/1989 | Daigle | |
| 5,083,004 A | 1/1992 | Wells et al. | |
| 5,153,519 A | 10/1992 | Wentworth et al. | |
| 5,153,673 A * | 10/1992 | Amirav | G01N 27/626 356/315 |
| 5,218,203 A | 6/1993 | Eisele et al. | |
| 5,394,092 A | 2/1995 | Wentworth et al. | |
| 5,541,519 A | 7/1996 | Stearns et al. | |
| 5,570,179 A | 10/1996 | Weckstrom | |
| 5,594,346 A | 1/1997 | Stearns et al. | |
| 5,611,846 A * | 3/1997 | Overton | G01N 30/64 73/23.36 |
| 5,612,489 A | 3/1997 | Ragsdale et al. | |
| 6,432,064 B1 * | 8/2002 | Hibner | A61B 10/0275 128/897 |
| 6,490,910 B1 | 12/2002 | Butler et al. | |
| 6,682,638 B1 | 1/2004 | Prohaska et al. | |
| 6,691,552 B2 | 2/2004 | Cardelius | |
| 7,013,707 B2 | 3/2006 | Prohaska et al. | |
| 7,493,795 B2 | 2/2009 | Komura et al. | |
| 7,586,092 B1 | 9/2009 | Karpetsky | |
| 7,736,908 B2 | 6/2010 | Prohaska et al. | |
| 7,812,614 B2 | 10/2010 | Kurita et al. | |
| 7,824,471 B2 | 11/2010 | Gamache et al. | |
| 7,902,498 B2 | 3/2011 | Miller et al. | |
| 8,123,396 B1 | 2/2012 | Karpetsky et al. | |
| 8,237,110 B2 * | 8/2012 | Peng | G01N 27/622 250/286 |
| 8,239,171 B2 | 8/2012 | Gamache et al. | |
| 2005/0230616 A1 * | 10/2005 | Cameron | G01N 27/624 250/287 |
| 2009/0031785 A1 | 2/2009 | Kellner et al. | |

FOREIGN PATENT DOCUMENTS

GB 2344655 A 6/2000

* cited by examiner

*Primary Examiner* — Laura Martin
*Assistant Examiner* — Alex Devito
(74) *Attorney, Agent, or Firm* — IPAXIO S.E.N.C.

(57) ABSTRACT

The micro-plasma emission detector unit is for use with a gas chromatograph. It includes an airtight housing having an internal ionization chamber and a makeup gas inlet chamber, a pair of spaced-apart ionization electrodes positioned on opposite sides of the ionization chamber, and a permeation device having a semi-permeable membrane. The semi-permeable membrane is at least partially and removably insertable through the makeup gas inlet chamber.

16 Claims, 8 Drawing Sheets

MICRO-PLASMA EMISSION DETECTOR UNIT AND METHOD

CROSS-REFERENCE TO RELATED APPLICATION

The present case claims the benefit of U.S. Patent Application No. 61/734,528 filed on 7 Dec. 2012, the content of which is hereby incorporated by reference in its entirety.

TECHNICAL FIELD

The technical field relates generally to micro-plasma emission detector units for use with gas chromatographs. It also relates to methods of conducting spectroscopic analyses of gas mixtures.

BACKGROUND

The basic chromatography is the separation of components of a sample owing to their differences in solubility or in adsorption in a stationary bed of a material (either liquid or solid). When the sample (moving phase) is a gas, the technique is referred to as gas-solid or gas-liquid chromatography, depending on whether the stationary phase is a solid or a liquid. In gas chromatography, a sample is introduced into a carrier gas as a vapor which flows through a chromatographic system. Upon separation by the stationary phase, the analytes travel through the gas chromatograph at different speeds and enter a detecting device, which device is connected to the gas chromatograph, at different times. As a result, individual analytes that are present in the sample may be identified by the detecting device.

The analytes transported carried using a carrier gas. The carrier gas is an inert gas for the analyte. Argon and helium are two examples of carrier gases. Other gases and mixtures of gases can be used as well, depending on the implementations and/or the requirements.

A same gas chromatograph can be used with different kinds of detecting devices, depending on the needs. The various kinds of detecting devices can themselves have different sensitivity levels. For instance, some detecting devices can be designed to detect very low concentrations of an analyte, such as in the range of parts per million (ppm). Others can be designed to detect concentrations in the range of a few percent or more.

Some detecting devices can measure the concentrations of analytes based on ionization. The carrier gas with the analytes is directed from the outlet of the gas chromatograph to an ionization chamber located in-between a pair of electrodes provided inside the detecting devices. The detecting device is designed to transform the carrier gas and each analyte into plasma using the electrodes. The plasma results in light radiations, including visible light. The light radiations can be sensed and recorded using a corresponding light sensor. The spectral content of the data obtained from the light sensor can reveal the presence of some analytes and their concentration.

In general, the size of a detecting device is a factor that can impact the operation of gas chromatographs. Larger detecting devices require more space next to the gas chromatograph and can also require a relatively high flow rate. A higher flow rate means that more carrier gas must be used and this increases operation costs. Still, minimizing the flow rate is further desirable given all the usual inherent difficulties in alleviating contamination of the carrier gas and the whole carrier gas circuit. Minimizing the size of detecting devices is thus generally desirable. It is also desirable to minimize the size of detecting devices since the available space around gas chromatographs can be limited.

Permeation devices for adding OH doping agent to the carrier gas are used in the field of gas chromatography to increase the accuracy of the measurement of analytes. Most permeation devices use water provided inside a semi-permeable membrane as a source of OH doping agent. For instance, adding, accurately adjusting and maintaining the level of water vapor in the carrier gas improves and/or stabilizes the carbon impurities that may be present in the carrier gas circuit, thereby allowing them to be measured. OH doping agents can partially reduce or even totally eliminate the carbon deposits that tend to adhere on the walls of the discharge zone. Over time, these carbon deposits can block the light radiations from the sensors and shorten the lifespan of the detecting device.

Various configurations and arrangements exist to provide OH doping agents in the carrier gas. Existing permeating devices require additional external hardware components and corresponding control systems. For instance, ovens can be used to provide heat for controlling the amounts of water vapor going through the semi-permeable membrane of the permeation device. However, this adds complexity and leaves less available space around the gas chromatograph. Relatively small permeation devices exist but these devices are tailored to specific concentrations and/or flow rates. They also have a limited lifespan since only a relatively small quantity of water is present therein and they cannot be refilled. Switching from one permeation device to another is generally a difficult task in gas chromatography.

Accordingly, there is still room for many improvements in this area of technology.

SUMMARY

In one aspect, there is provided a micro-plasma emission detector unit for use with a gas chromatograph, the detector unit including: an airtight housing having an internal ionization chamber, the housing including a carrier gas inlet and a gas outlet that are in fluid communication with the ionization chamber through internal passageways, the housing further including a makeup gas inlet and a makeup gas inlet chamber, the makeup gas inlet chamber being in fluid communication with the carrier gas inlet upstream the ionization chamber, and at least one light collection window area in registry with the ionization chamber; a pair of spaced-apart ionization electrodes provided in the housing and positioned on opposite sides of the ionization chamber; and a permeation device containing a semi-permeable membrane, the semi-permeable membrane being at least partially and removably insertable inside the makeup gas inlet chamber.

In another aspect, there is provided a method of conducting spectroscopic analyses of gas mixtures, the method including the simultaneous steps of: receiving a stream of carrier gas from a gas chromatograph into a housing, the carrier gas stream containing at least one analyte; receiving a makeup gas stream into the housing; mixing the makeup gas stream with an OH doping agent coming from a semi-permeable membrane located at least partially inside a chamber of the housing; mixing the carrier gas stream with the makeup gas stream inside the housing to form a mixed gas stream; creating a plasma emission with the mixed gas stream inside the housing; measuring a light radiation resulting from the plasma; channeling the mixed gas stream out of the housing; and controlling the OH doping agent by monitoring and adjusting the temperature of the chamber in the housing in which the semi-permeable membrane is located.

Details on these aspects as well as other aspects of the proposed concept will be apparent from the following detailed description and the appended figures.

DETAILED DESCRIPTION

Figure 1:
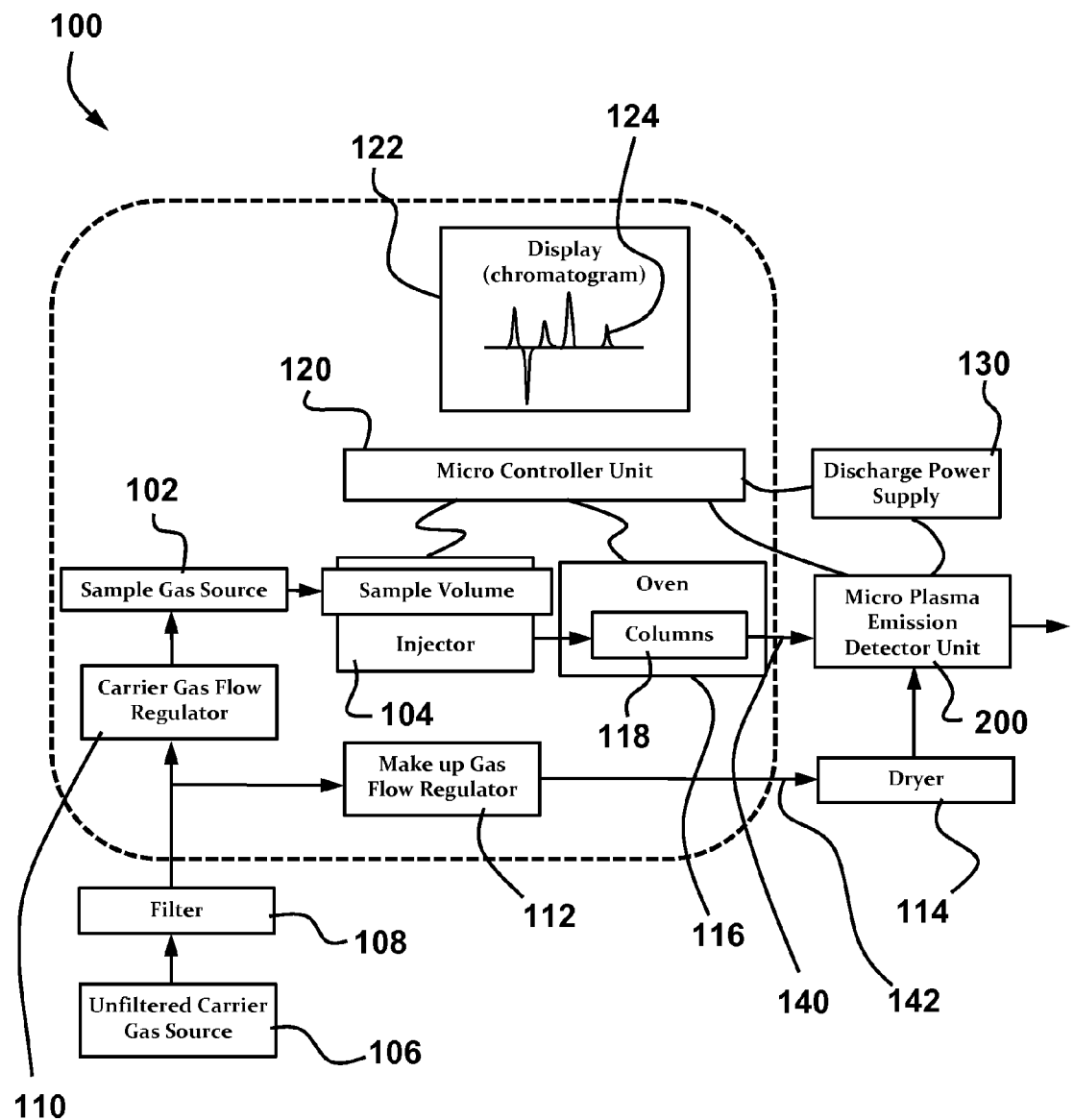
FIG. 1 is a schematic view illustrating a generic example of a gas chromatograph that can be used with a micro-plasma emission detector unit incorporating the proposed concept.

FIG. 1 is a schematic view illustrating a generic example of a gas chromatograph 100 that can be used with a micro-plasma emission detector unit incorporating the proposed concept. Other kinds of gas chromatographs, configurations and arrangements exist.

In the illustrated example, the gas chromatograph 100 receives a gas sample from a sample gas source 102. The gas sample coming from the sample gas source 102 is injected at an injector 104. The gas sample contains one or more analytes. Each analyte is a chemical compound to be analyzed.

The various components inside and outside the gas chromatograph 100 are in fluid communication with one another using a network of conduits or passageways. An example of such network is schematically illustrated in FIG. 1. Variants are possible as well.

In the illustrated example, the gas chromatograph 100 receives a carrier gas from an unfiltered carrier gas source 106, for instance one or more pressurized gas bottles. The analyte or analytes will be transported using the carrier gas. The carrier gas is an inert gas for the analyte or analytes. Argon and helium are two examples of carrier gases. Other gases and mixtures of gases can be used as well, depending on the implementations and/or the requirements.

In the illustrated example, the carrier gas coming from the carrier gas source 106 is filtered using a filter 108. The exact nature and construction of the filter 108 can vary from one implementation to another. It can also depend on the quality of the carrier gas from the carrier gas source 106. The filter 108 ensures that the carrier gas stream is substantially free of contaminants. This promotes the stability of the readings and the sensitivity of detection.

From the filter 108, the carrier gas is sent to a carrier gas flow regulator 110. A portion of the carrier gas will also be used as makeup gas in the illustrated example. The makeup gas goes through a makeup gas flow regulator 112 and then through a dryer 114. The dryer 114 removes substantially any remaining water vapor still present in the makeup gas, if any. The dryer 114 can be part of the gas chromatograph 100 or not. The dryer 114 can be used at ambient temperature or be heated using a heat source. It can include for instance dehydrated zeolite or a Zr—Vn—Fe alloy to capture any trace of residual OH doping agents. Variants are also possible as well. The dryer 114 can be omitted in some implementations or be located elsewhere.

In the illustrated example, the carrier gas flow regulator 110 is connected to the injector 104. The gas sample, once injected at the injector 104, is sent to an oven 116 having one or more gas separation columns 118. Each analyte will leave the column or columns 118 at different times. Thus, some analytes will get sooner out of the column or columns 118 than others, thus sooner out of the gas chromatograph 100.

A micro-plasma emission detector unit 200 is provided to measure the presence of one or more analytes and their concentration in the carrier gas stream at the outlet of the gas chromatograph 100. The detector unit 200 is located directly on the side of the gas chromatograph 100 in the illustrated example. Other arrangements and configurations are also possible.

The carrier gas outlet of the gas chromatograph 100 is depicted in FIG. 1 at 140. The makeup gas outlet of the gas chromatograph 100 is depicted in FIG. 1 at 142.

Figure 2:
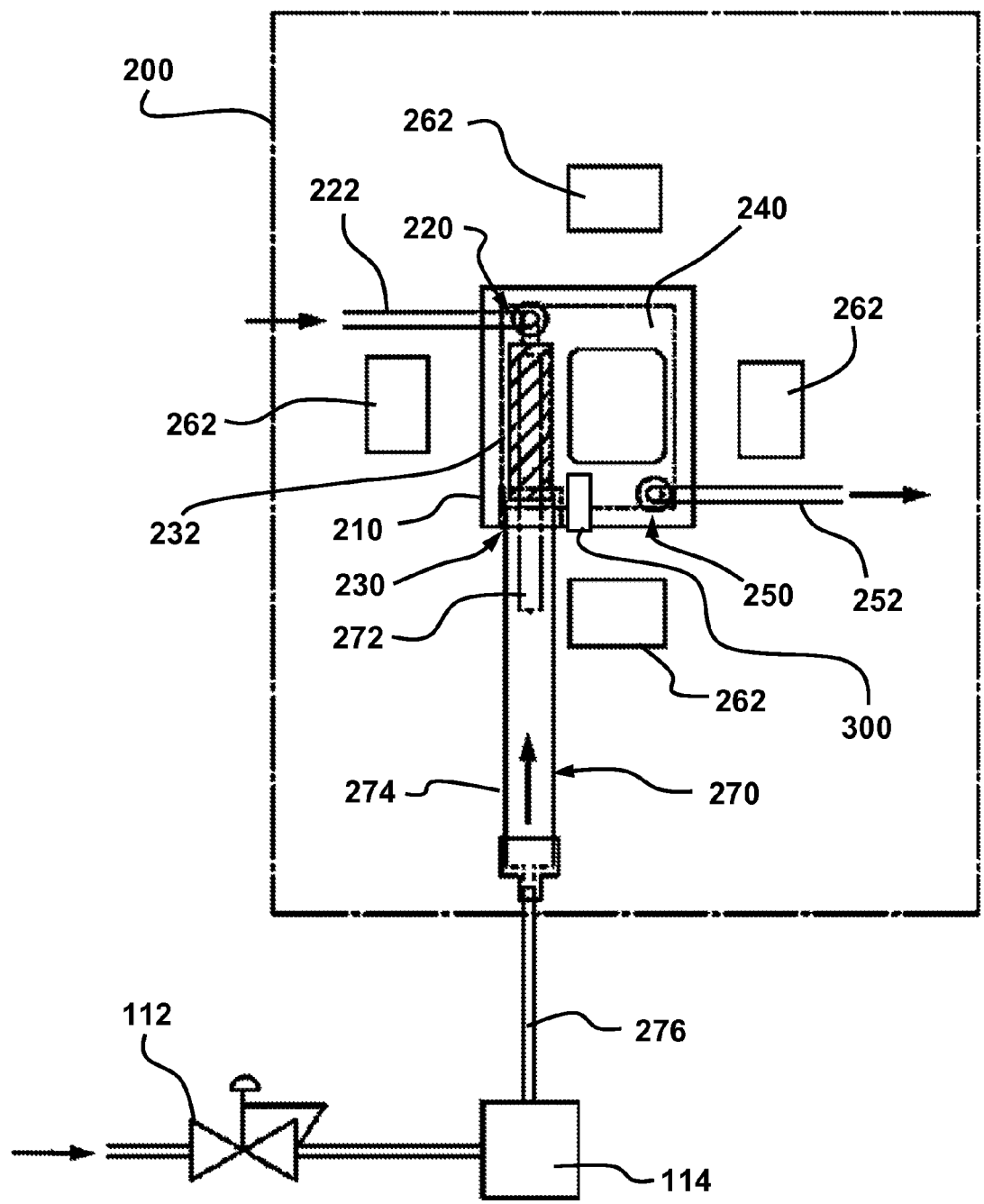
FIG. 2 is a semi-schematic view illustrating an example of a micro-plasma emission detector unit incorporating the proposed concept.

FIG. 2 is a semi-schematic view illustrating an example of a micro-plasma emission detector unit incorporating the proposed concept. Variants thereof are possible. Nevertheless, this example will now be referred to as the detector unit 200 for the sake of clarity. The detector unit 200 is also shown in FIGS. 3 to 7.

The carrier gas and the analyte or analytes coming from the column or columns 118 of the gas chromatograph 100 are sent to an ionization chamber 240 located inside the detector unit 200.

The detector unit 200 is designed to transform the carrier gas and each analyte into plasma using a pair of electrodes 290, 292 (FIG. 7) provided inside the detector unit 200. The plasma results in light radiations, including visible light. The spectral content will reveal the presence of a given analyte and its concentration. The ionization chamber 240 is provided between the two workpieces 212, 214 in the illustrated example.

In use, the detector unit 200 receives the analyte or analytes from the gas chromatograph 100 at different times, for instance over the course of a few minutes from the time the gas sample was injected at the injector 104 until its entire content went through the column or columns 118. The light radiation resulting from the plasma will vary from one analyte to another, thus over the given time period. Data regarding the light radiations will be recorded throughout this process.

In the illustrated example, the gas chromatograph 100 includes a micro-controller unit 120 for controlling the different components, for instance the carrier gas flow regulator 110, the makeup gas flow regulator 112, the oven 116, various valves that can be provided on the network of conduits and passageways, and the detector unit 200. The micro-controller unit 120 can also record data from the detector unit 200. Variants are possible as well.

Also in the illustrated example, the data signals received from the detector unit 200 can be in the form of analog signals and these signals can be converted to digital signals by the micro-controller unit 120 before being transferred to another device, for instance a computer system or the like. The micro-controller unit 120 can also analyze these data signals and display chromatograms, for instance using a computer screen 122 as shown in FIG. 1. An example of a chromatogram 124 is shown. The chromatogram 124 is a visual representation of the spectral content of the light radiation received from the plasma over the time period.

FIG. 1 also shows that the detector unit 200 of the illustrated example is connected to a discharge power supply 130. The discharge power supply 130 is designed to provide AC or DC voltage at given frequencies, for instance between 60 Hz and 100 kHz, to the electrodes inside the detector unit 200. This discharge power supply 130 can be controlled and provided in electrical energy using the micro-controller unit 120, as shown. For instance, the micro-controller unit 120 can provide a DC voltage between more than 0 to 12 V DC at the primary side of the discharge power supply 130. Other values are also possible. The secondary side of the discharge power supply 130 will provide the higher voltage to the electrodes 290, 292 so as to create the plasma discharges inside the detector unit 200. The discharge power supply 130 is connected to the detector unit 200 using corresponding electric cables or the like. The exact construction, configuration and operational parameters of the discharge power supply 130 can vary from one implementation to another.

The detector unit 200 includes an airtight housing 210 having a plurality of internal chambers and passageways. The illustrated housing 210 has a substantially rectangular outer shape. Variants are possible. For instance, the housing 210 can have a triangular or hexagonal shape, to name just a few. Many other variants are possible. The housing 210 can be made very small, for instance having a few millimeters in size.

The housing 210 includes a carrier gas inlet 220, a makeup gas inlet 230, the internal ionization chamber 240 and a gas outlet 250. The carrier gas inlet 220 is connected to the carrier gas outlet 140 of the gas chromatograph 100 using a carrier gas inlet conduit 222. In the illustrated example, the carrier gas inlet conduit 222 has an upstream end in direct fluid communication with the outlet of the column or columns 118, and a downstream end connected directly to the carrier gas inlet 220. The carrier gas inlet conduit 222 is inserted into a carrier gas inlet chamber 224 that acts as a socket.

The various connections at the carrier gas inlet 220, the makeup gas inlet 230 and the gas outlet 250 of the detector unit 200 with other components can include gaskets, seals and/or layers of epoxy or the like to make all links air tight and thereby mitigating contamination risks. The carrier gas inlet 220, the makeup gas inlet 230 and the gas outlet 250 have a circular cross section in the illustrated example. Variants are possible.

The carrier gas inlet 220, the makeup gas inlet 230 and the gas outlet 250 are in fluid communication with the ionization chamber 240 through internal passageways. The makeup gas inlet 230 of the illustrated example is in fluid communication with the carrier gas inlet 220 at a location upstream the ionization chamber 240. The gases coming out of the detector unit 200 through the gas outlet 250 are sent into an outlet conduit 252 before being discarded. Variants are possible.

In use, the temperature of the various parts of the housing 210 can fluctuate greatly and can become very high. The housing 210 must still remain air tight at all times in spite of the thermal expansions and contractions. The housing 210 of the illustrated example is provided as a monolithic block to address this challenge. It is made of a dielectric material that allows maximum inertness to the analyte or analytes. It is also transparent, particularly to ultraviolet (UV) light radiations. Examples of possible materials include quartz, borosilicate, industrial grade sapphire and synthetic diamond. These materials allow good light transmission from UV to infrared spectrum. Other materials are possible.

In the illustrated example, the material used is highly-purified synthetic quartz. Such material can have a response of about 80% in the spectral range between 200 and 2500 nm. Melted natural crystalline quartz offers a response of about 80% in the spectral range between 230 and 3500 nm and thus, can also be used as a material for the housing 210. These materials offer a relatively large spectral response and are fusible. Nevertheless, variants are possible as well.

The monolithic block of the illustrated housing 210 was obtained using two distinct synthetic quartz workpieces, namely a first workpiece 212 and a second workpiece 214. The first workpiece 212 was made thicker than the second workpiece 214 in this example. These workpieces 212, 214 were machined separately using high precision manufacturing techniques since they are generally relatively small in size. They were later fused together at a high temperature to ensure a permanent and perfect interconnection between their corresponding major sides. Once fused, the two workpieces 212, 214 form the monolithic block. It is desirable that the junction between the two workpieces 212, 214 must not be visible once they are fused, i.e. be seamless. Adhesives are often unsuitable for fusing the two workpieces 212, 214 together since adhesives will most likely not resist the various chemical products and are also prone to deterioration at high temperatures in this specific context. Nevertheless, variants are still possible.

The side or sides of the housing 210 include at least one light collection window area 260 (FIG. 5) that is in registry with the ionization chamber 240. The rectangular-shaped housing 210 of the illustrated detector unit 200 includes four light collection window areas 260. These light collection window areas 260 are directly integrated into the monolithic block in the illustrated example. Thus, no additional parts are required. This is highly desirable since it greatly simplifies the airtightness of the housing 210. Nevertheless, variants are possible. One can also use more or less than four light collection window areas 260, depending on the needs and the outer shape of the housing 210.

The wall at each light collection window area 260 must be substantially free from imperfections and have a high degree of flatness, for instance being less than 0.002 mm (2 µm), to optimize the light transmission. The light collection window areas 260 of the illustrated example are also substantially perfectly flat surfaces to alleviate light reflection and/or diffusion. Imperfections could otherwise result in a loss in the amount of light radiations being transmitted through the wall of a given light collection window area 260 and this can decrease the sensitivity of the detector unit 200 for one or more analytes.

The illustrated detector unit 200 includes four light sensors 262, one for each light collection window area 260. The aperture of the light sensors 262 are positioned to be in registry with the corresponding light collection window area 260. If required, each light sensor 262 can include an optical interference filter or a combination of multiple optical interference filters for blocking undesired spectral bands, depending on the measurement type and the spectral bands of interest. The exact type and nature of these interference filters, if they are required, can vary from one implementation to another. The interference filters can even be different from one light sensor to another within the same detector unit 200. Each interference filter can be directly mounted in front of the aperture of the corresponding light sensor 262 so as to be parallel to the corresponding light collection window area 260. Each interference filter can also be very close to its corresponding light collection window area 260, for instance at a distance between 0 to about 10 mm from the corresponding light collection window area 260. The interference filters can also be integrated inside the light sensors 262 and they could be omitted in some implementations. The light sensors 262 can be positioned very close to the corresponding light collection window areas 260, for instance at a distance between 0 to about 10 mm from the corresponding light collection window area 260.

Each light sensor 262 can include a photodiode, for instance a UV enhanced type photodiode to increase the sensitivity level from the low UV light spectrum up to the infrared (IR) light spectrum. Other kinds of devices are possible. Each light sensor 262 can further include a low-noise electronic circuitry on which the photodiode is mounted. This circuitry can include a high gain amplifier that converts current signal to voltage signal. The circuitry and the photodiode can be provided inside a protective housing and then set directly in front of the corresponding light collection window area 260, with or without the interference filter between them.

As can be appreciated, the suggested arrangement can be made without using mirrors and/or prisms to collect the light, all of which can increase costs and complexity. The response is also much better with a direct light transmission. Still, the suggested arrangement provides an increased aperture size to collect the light when compared, for instance, to optical fibers or the like. The width of the light collection window areas 260 in the illustrated example can be for instance between 1 and 7 mm. Variants are also possible.

The makeup gas can be supplied into the detector unit 200 using a makeup gas inlet conduit 276 that is connected to the makeup gas outlet 142 of the gas chromatograph 100. As shown in FIG. 2, the detector unit 200 includes a permeation device 270 to provide an accurate amount of OH doping agent in the makeup gas to increase the accuracy of the measurement of analytes. The downstream end of the makeup gas inlet conduit 276 is removably connected to the inlet end of the permeation device 270. The permeation device 270 includes water inside a semi-permeable membrane 272 forming an elongated pocket and that is coaxially disposed within a rigid outer tube 274, for instance a tube made of metal. The permeation device 270 is thus substantially configured in the form of a cartridge. Variants are also possible.

In the illustrated example, the semi-permeable membrane 272 extends out of the end of the rigid outer tube 274. With the semi-permeable membrane 272, the higher the temperature is, the higher the permeation rate is. The rigid outer tube 274 can be attached and sealed to the carrier gas inlet 230 of the housing 210 using for instance a high temperature and chemical resistant epoxy. Variants are also possible.

In use, the makeup gas is first sent through the permeation device 270 when entering the detector unit 200. However, before going into the detector unit 200, the makeup gas from the makeup gas flow regulator 112 of the illustrated example goes through the dryer 114. Using the dryer 114, the OH doping agent level can be made very stable and accurate since it could be assumed that no remaining water vapor will be present in the makeup gas. Variants are also possible.

As can be seen in FIG. 2, the semi-permeable membrane 272 is at least partially insertable through the makeup gas inlet 230 and into a makeup gas inlet chamber 232 provided inside the housing 210 of the detector unit 200. In the illustrated example, the makeup gas inlet chamber 232 includes a first portion adjacent to the carrier gas inlet 230 and having a larger inner diameter than that of a second portion located downstream the first portion. The first and second portions are coaxially disposed with reference to one another. The first portion acts as a socket for the rigid outer tube 274. The inner diameter of first portion matches the outer diameter of the rigid outer tube 274 for a tight fit. The semi-permeable membrane 272, however, can still be easily removed from the housing 210 and from the permeation device 270 when needed. This arrangement is made so that the semi-permeable membrane 272 can be easily replaced when required, for instance when empty or to change the level of OH doping agents. The semi-permeable membrane 272 of the illustrated permeation device 270 extends into the makeup gas inlet chamber 232, thus inside the housing 210.

Figure 3:
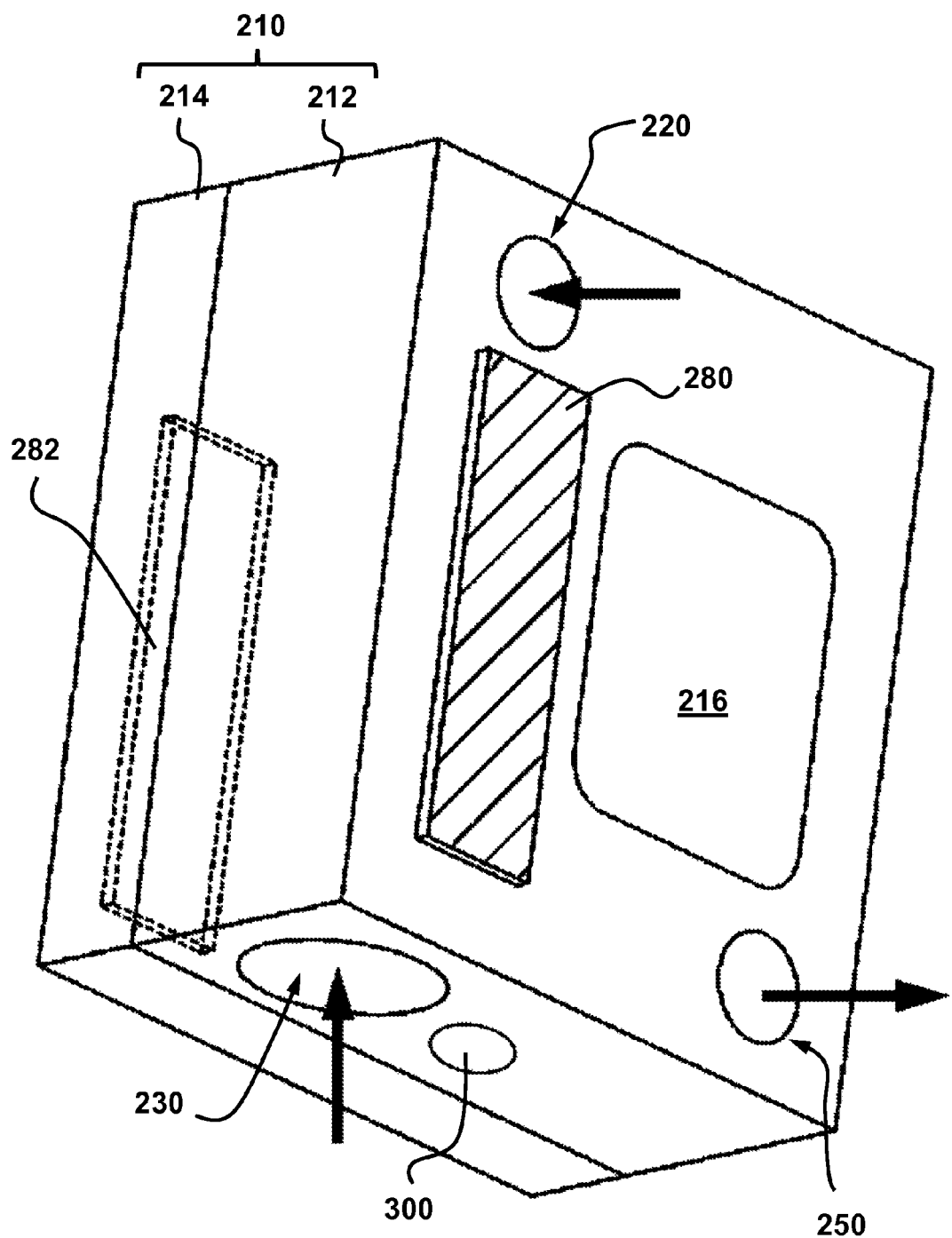
FIG. 3 is a top isometric view of the housing and the integrated heater elements of the detector unit shown in FIG. 2.

One or more electric heater elements can be provided directly on the outer surface of the housing 210 to adjust the temperature. Increasing the temperature will increase the OH doping agents. Conversely, providing less heat will decrease the OH doping agents. As shown in FIG. 3, the illustrated housing 210 includes two electric heater elements 280, 282. Each heater element 280, 282 can include a metal layer attached to a corresponding outer surface of the housing 210, for instance a metal layer adhesively attached thereon using epoxy or the like. The metal layer can be made for instance using a film formed by metal deposition. This film can be made of material selected from the group consisting of silver, aluminum, copper, brass and alloys thereof. This arrangement makes the detector unit 200 very compact. Variants are possible as well.

The electric power supply to the heater elements 280, 282 can be controlled by the micro-controller unit 120. The temperature inside the makeup gas inlet chamber 232 can be sensed using a temperature sensor 300 inserted in a corresponding chamber machined on the side of the housing 210. This chamber is adjacent to the makeup gas inlet chamber 232. The temperature sensor 300 can provide feedback signals to the micro-controller unit 120. Other configurations and arrangements are also possible.

Figure 4:
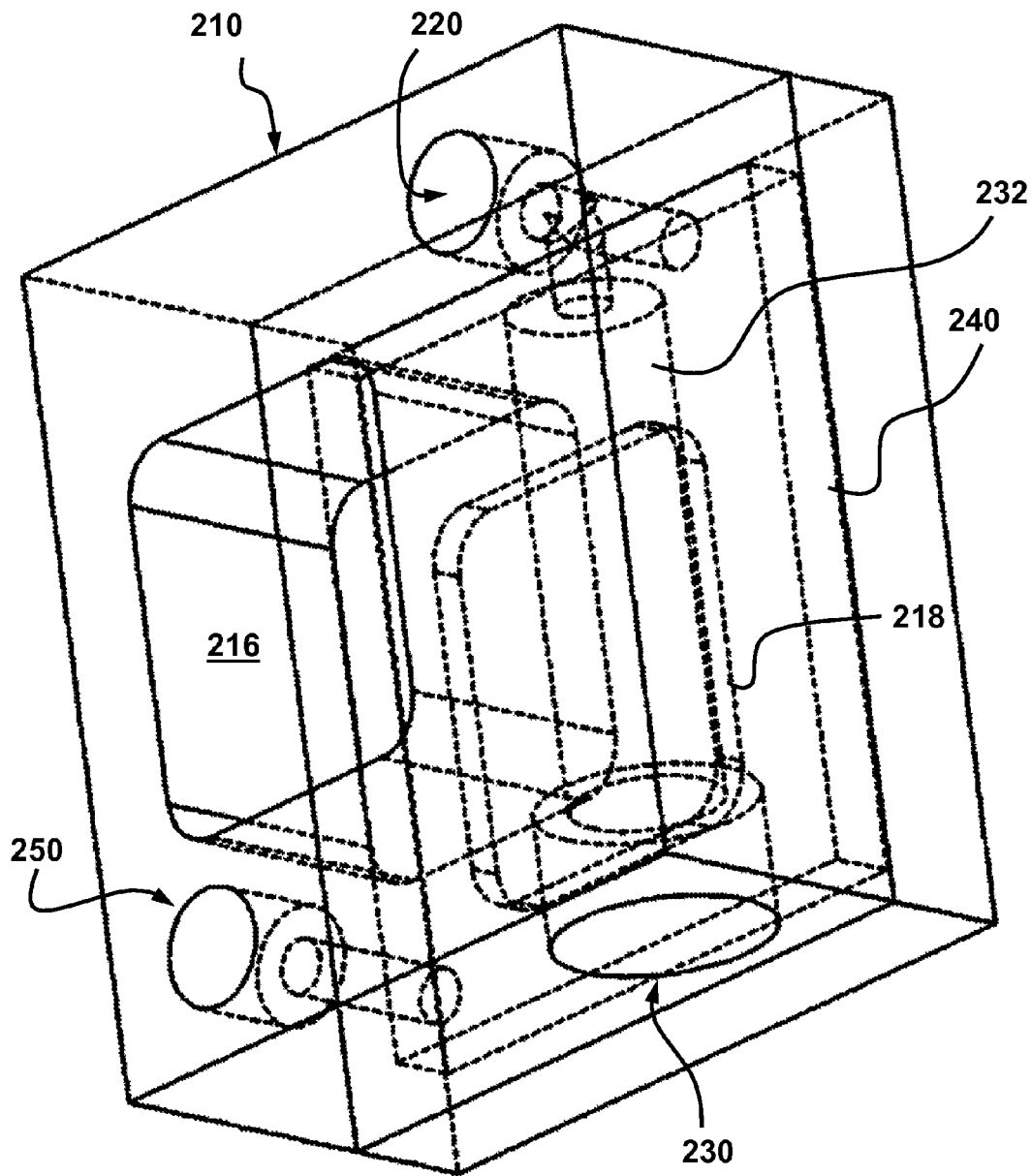
FIG. 4 is a bottom isometric view of the housing of the detector unit shown in FIG. 2.

FIG. 4 is a bottom isometric view illustrating the housing 210 of the detector unit 200. The interior of the housing 210 in this figure is visible to show the details thereof.

Figure 5:
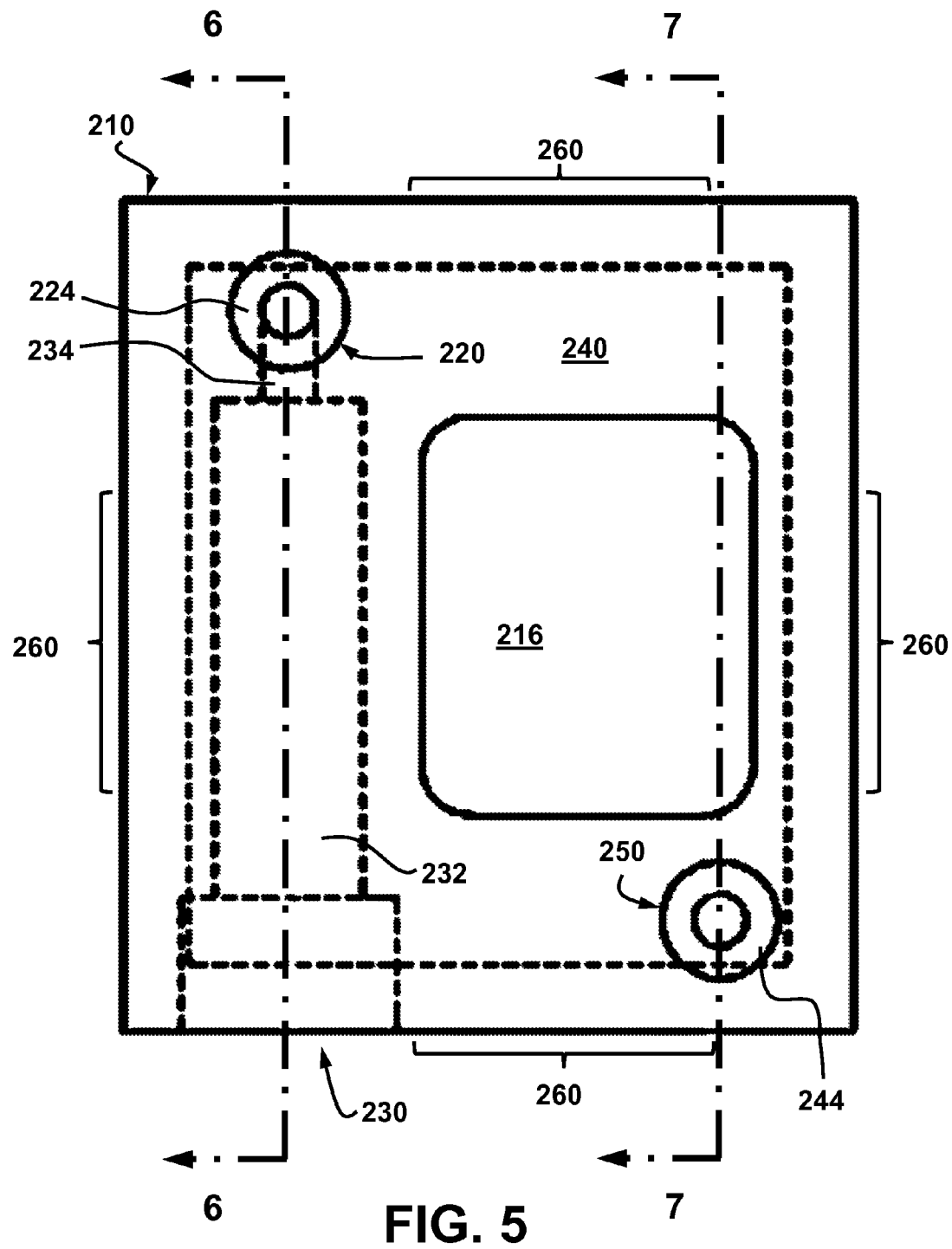
FIG. 5 is a top plan view of the housing of the detector unit shown in FIG. 2.
Figure 6:
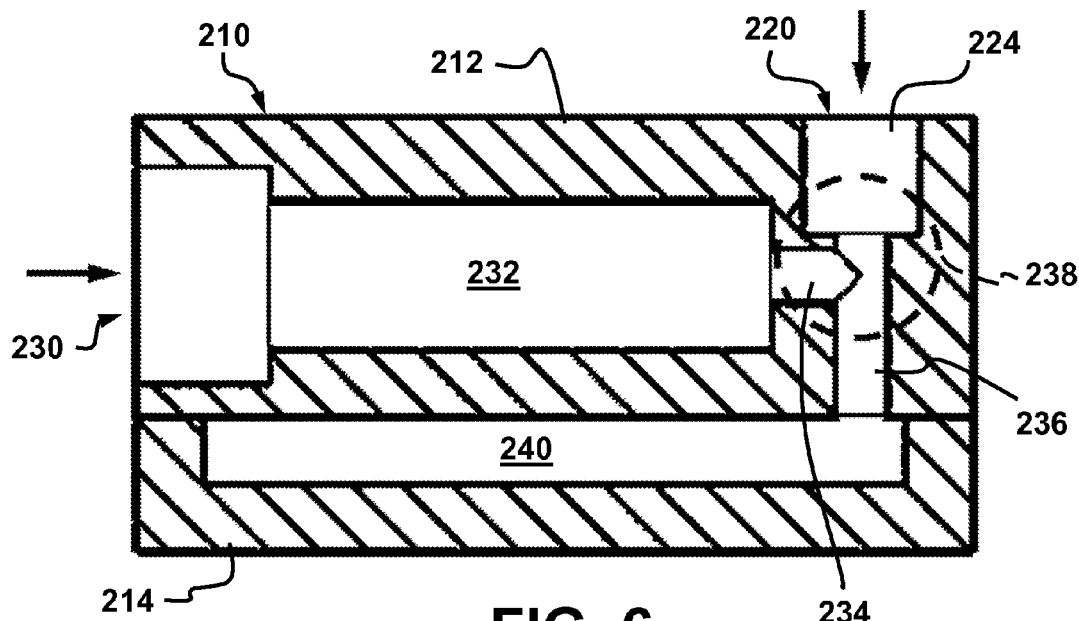
FIG. 6 is a first cross-sectional view of the housing taken along line 6-6 in FIG. 5.
Figure 7:
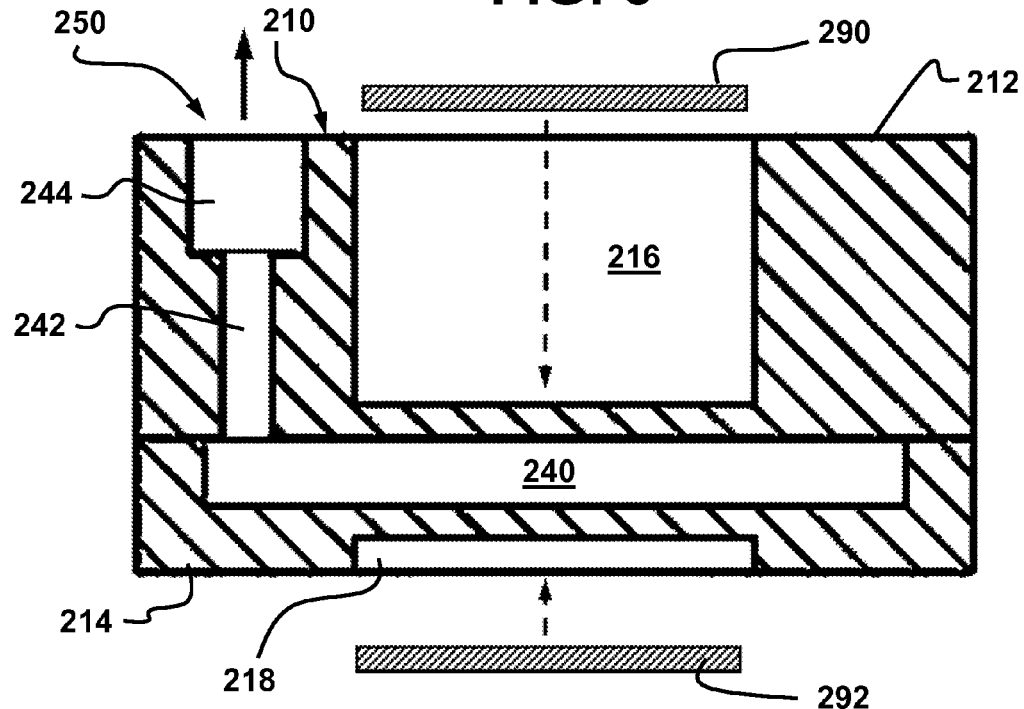
FIG. 7 is a second cross-sectional view of the housing taken along line 7-7 in FIG. 5.

FIG. 5 is a top plan view of the housing 210 of the detector unit 200. This figure shows where the lines for the cross-sectional views of FIGS. 6 and 7 are taken. FIG. 5 also shows the ionization chamber 240 and the location of the four light collection window areas 260 of this detector unit 200. Each light collection window area 260 can be a given area of a corresponding side wall of the second workpiece 214 and/or be delimited by a machined area inside and/or outside the ionization chamber 240 to make the wall thinner at this area. The wall portions outside the light collection window areas 260 can be coated and/or be otherwise covered to restrict and/or to completely prevent light transmission through these other wall portions.

FIG. 6 is a first cross-sectional view of the housing 210 taken along line 6-6 in FIG. 5. This figure shows the makeup gas inlet 230, the makeup gas inlet chamber 232, the carrier gas inlet 220 and the ionization chamber 240. As aforesaid, the makeup gas inlet chamber 232 is configured and disposed to receive entirely or at least a portion of the semi-permeable membrane 272 once the permeation device 270 is in position. The downstream end of the permeation device 270 is thus located directly inside the housing 210. The semi-permeable membrane 272 is located between the heater elements 282 and heat from the heater elements 280, 282 can then quickly and directly reach the semi-permeable membrane 272 in a very efficient manner. This way, the control and the stability of the OH doping agents can be more accurately controlled than ever before due to the compact design and the monolithic block construction.

In the illustrated example, the downstream end of the makeup gas inlet chamber 232 is in fluid communication with the carrier gas inlet 220 through a first narrow passageway 234 machined into the first workpiece 212. In use, the first passageway 234 will receive the makeup gas from the makeup gas inlet chamber 232, in which an accurate mixture of the makeup gas and OH doping agents is created. The first passageway 234 intersects a second narrow passageway 236 at right angle. This second passageway 236 extends between the carrier gas inlet 220 and the ionization chamber 240. The carrier gas stream and the makeup gas stream will thus mix to form a mixed gas stream around an intersection zone 238. The carrier gas and the analyte or analytes to be measured come through the carrier gas inlet conduit 222 into the carrier gas inlet 220 and are gently mix with the makeup gas at the intersection zone 238 without passing through any dead volume zone. The accuratcly of the measurements inside the ionization chamber 240 will be much better. It is a very desirable advantage compared to existing technology where internal dead volumes are present. The passageways 234, 236 also offer the possibility of operating at relatively low flow rates without creating phantom peaks or baseline instability in the chromatograms. Variants are also possible.

As best shown in FIG. 6, the ionization chamber 240 of the illustrated housing 210 is formed by a cavity machined into the inner major face of the second workpiece 214 before it was fused with the inner major face of the first workpiece 212. The inner major face of the first workpiece 212, which is flat in the illustrated example, closes the top side of the ionization chamber 240. Variants are also possible as well.

FIG. 7 is a second cross-sectional view of the housing 210 taken along line 7-7 in FIG. 5. This figure shows the ionization chamber 240 and also the gas outlet 250 from which the waste gases are conveyed out of the ionization chamber 240 through a third narrow passageway 242 made inside the first workpiece 212 of the illustrated example. The first passageway 242 leads into an outlet chamber 244 having a larger diameter and that is a socket for the outlet conduit 252. The outlet passageway 242 and the outlet chamber 244 are designed with inner diameters that are large enough to avoid a pressure built up in the ionization chamber 240. This design improves the stability of the flow inside the ionization chamber 240 and/or mitigates the pressure fluctuations during the operations.

The electrodes 290, 292 are provided to create the plasma are shown in FIG. 7. In the illustrated example, both electrodes 290, 292 are inserted into corresponding opened cavities 216, 218 made on the housing 210. The first cavity 216 for the first electrode 290 in the first workpiece 212 is significantly deeper than the second cavity 218 for the second electrode 292 made in the second workpiece 214. This way, once in position, both electrodes 290, 292 can be mounted at equal distance on opposite sides of the ionization chamber 240. The walls separating the electrodes 290, 292 from the ionization chamber 240 must be from 0.5 mm up to 5 mm in thickness, more precisely in a range of 0.5 to 2.5 mm. These walls are made of a dielectric material. Alternatively, the electrodes 290, 292 can include an electric insulation. Variants are also possible. For instance, the electrodes 290, 292 can be located at unequal distances from the ionization chamber 240 in some implementations.

The electrodes 290, 292 can be made of a material selected from the group consisting of aluminum, brass, copper, silver and alloy thereof. Variants are possible as well.

In use, the OH doping agents can be adjusted, for instance by changing the temperature of the housing 210 and that of the makeup gas inlet chamber 232 using the integrated heater elements 280, 282 of the illustrated example. The flow rate of OH doping agents can also be changed when the flow rate of the makeup gas is changed using the makeup gas flow regulator 112. Moreover, the size and the material inside the semi-permeation membrane 272 can be selected to obtain the desired level of OH doping agent. The fact that the semi-permeable membrane 272 can be easily replaced by another one is an interesting advantage. By adjusting the flow rate, the temperature inside the permeation device 270, the permeation membrane size and permeation membrane material, the amount of OH doping agents can be accurately selected as desired without the need of changing hardware components in the gas chromatograph 100.

Figure 8:
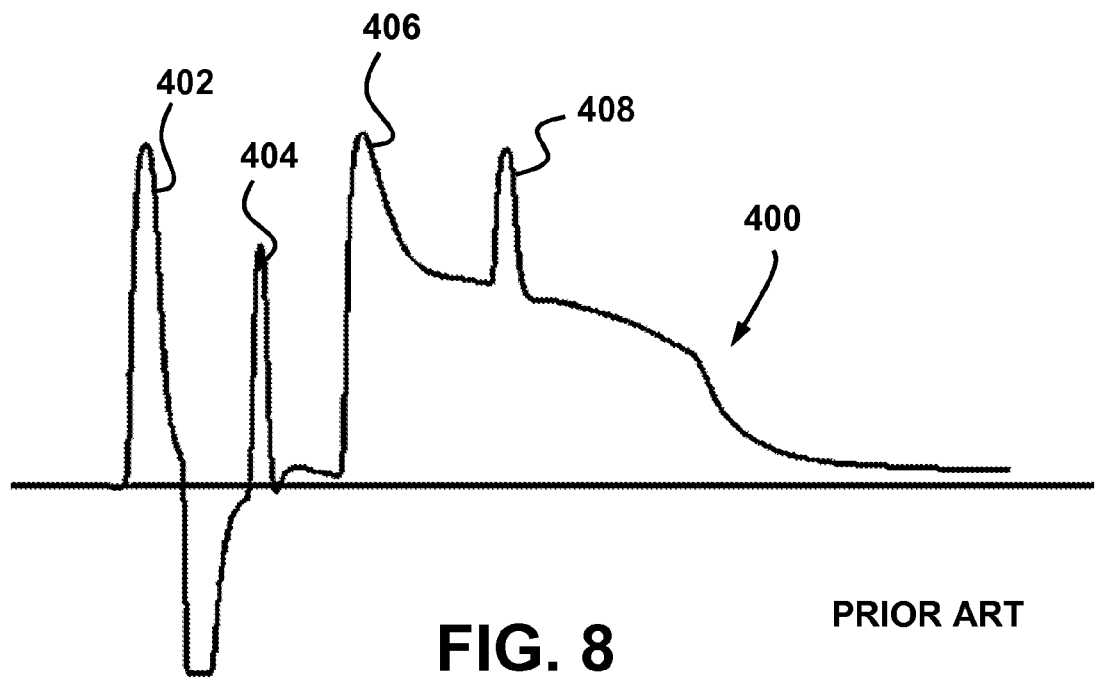
FIG. 8 shows a graph depicting a first example of a chromatogram for a gas sample obtained from a detecting device of the prior art.

FIG. 8 shows a graph 400 depicting a first example of a chromatogram using a detecting device of the prior art. In this example, the sample gas contains 1% weight of hydrogen ($H_2$), 1% weight of oxygen ($O_2$), 1% weight of nitrogen ($N_2$), 1% weight of methane ($CH_4$) and 1% weight of carbon monoxide (CO). Graph 400 shows peaks 402, 404, 406, 408 that are not clearly quantifiable or measurable due to the fact that the peaks are not shaped as Gaussian peaks. Gaussian peaks are highly desirable in gas chromatography for the integration and calculation of the peak area. Poor results often require a correction, for instance by reducing the sample volume injected. This can correct peak shapes and result in peaks having a Gaussian shape. However, this correction technique requires manually changing hardware parts in the gas chromatograph 100, thereby increasing time and costs. Moreover, reducing the sample volume impacts the lowest concentration that the detector unit 200 can detect, thus its operating range.

Figure 9:
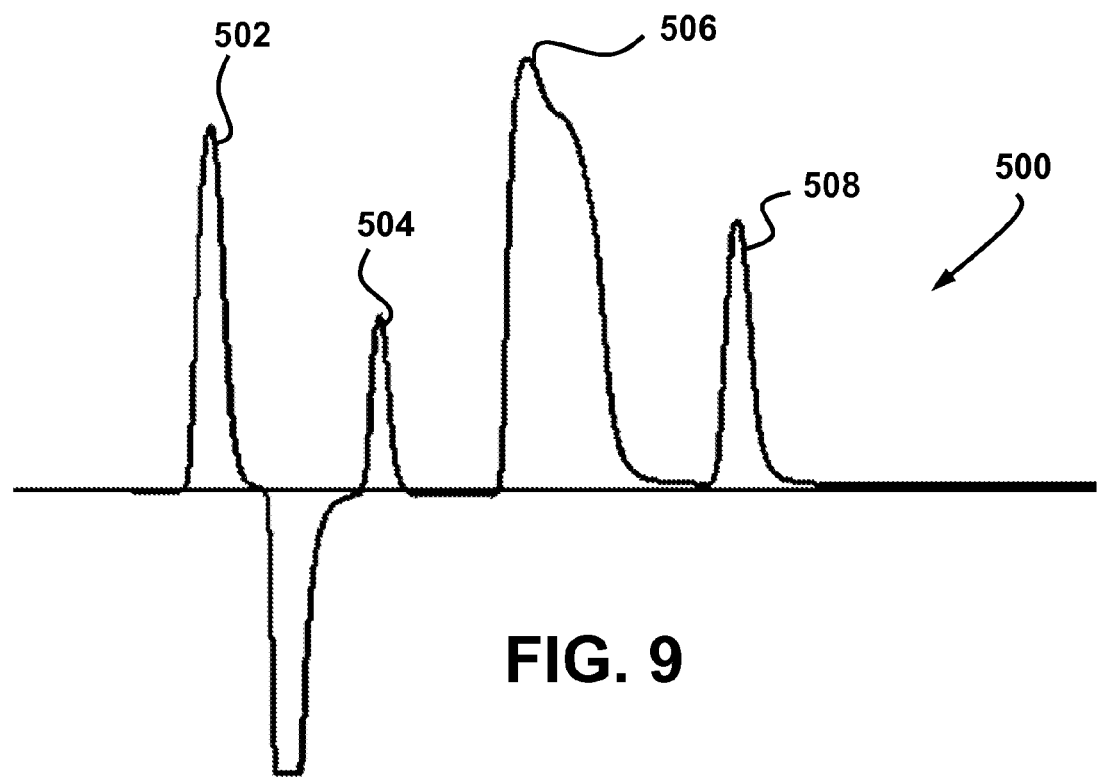
FIG. 9 shows a graph depicting a second example of a chromatogram obtained using the detector unit as suggested herein for the same gas sample as in FIG. 8, but using deliberately-inaccurate amounts of OH doping agent for the purpose of illustration.

FIG. 9 shows a graph 500 depicting a second example of a chromatogram. This graph 500 was obtained using the detector unit 200 as suggested herein for the same gas sample as in FIG. 8. However, deliberately inaccurate amounts of OH doping agent were used for the purpose of illustration. The equilibrium of OH is not adequate and the peaks 502, 504, 506, 508 are not perfectly Gaussian. For instance, the $CH_4$ peak 506 clearly demonstrates a tailing at the end of the peak. When carbon analytes are involved, carbon tend to adhere to the wall surfaces inside the housing 210, which results of a tailing on the carbon impurities when they eventually pass through the detector unit 200.

Figure 10:
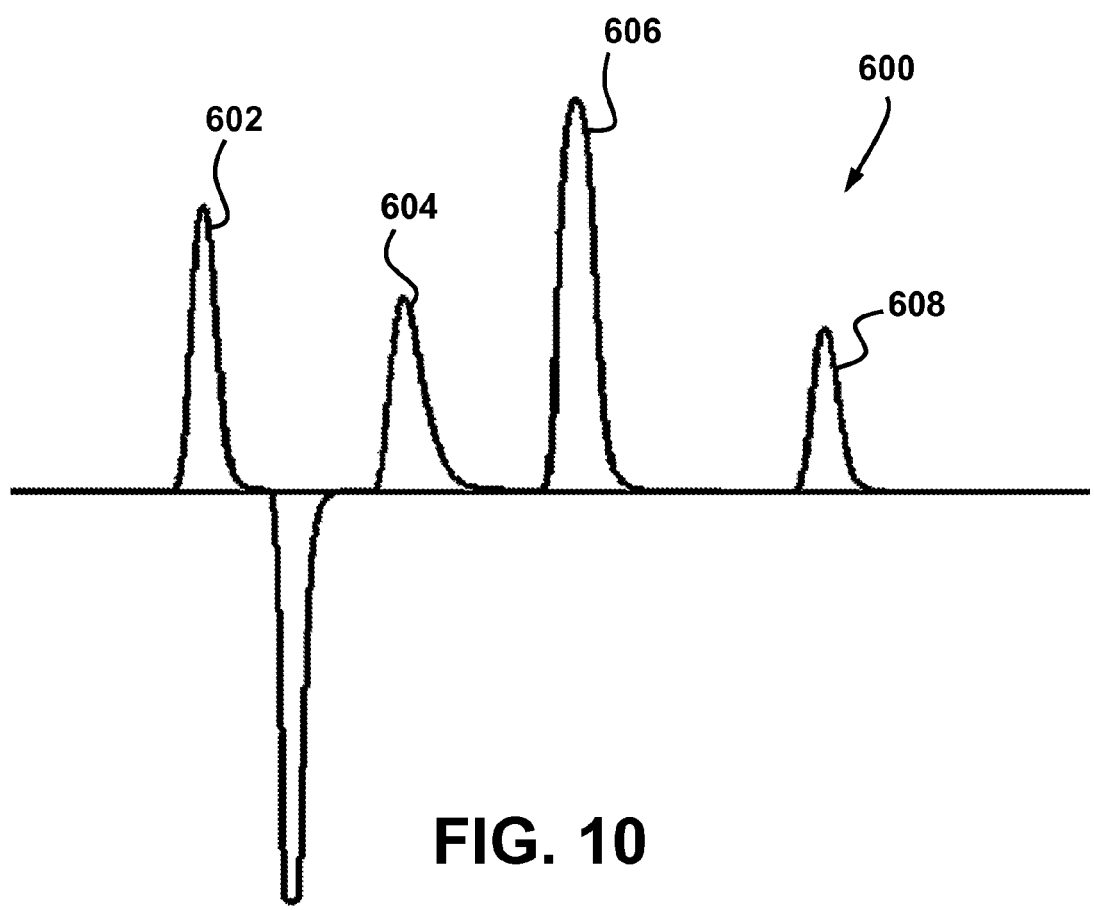
FIG. 10 shows a graph depicting a third example of a chromatogram obtained using the detector unit as suggested herein for the same gas sample as in FIGS. 8 and 9, but using a right amount of OH doping agent.

FIG. 10 shows a graph 600 depicting a third example of a chromatogram obtained using the detector unit 200 for the same gas sample as in FIGS. 8 and 9, but this time using a right amount of OH doping agent. Using the right equilibrium of OH doping agent allows measurements of all the impurities including the carbons. The measured peaks 602, 604, 606, 608 are then perfectly Gaussian and can then be perfectly quantified by chromatography. The $H_2$ peak 602, the $N_2$ peak 604, the $CH_4$ peak 606 and the CO peak 608 are now clearly visible.

Overall, using the proposed concept, making linear and very accurate measurements are now possible even in presence of high levels of impurities, all this without the need of modifying hardware components of the gas chromatograph 100. The same detector unit 200 can be used either for low ppb measurements or measurements in presence of high impurity levels using the same compact hardware, simply by changing the rate of OH doping agent, for instance by modifying the operating temperature of the housing 210 and/or using a different semi-permeable membrane 272. A higher temperature operation of the permeation device 270 and its semi-permeable membrane 272 will allow higher impurities level measurement and ensure linearity and Gaussian peaks shape since the level of OH doping agent going through the discharge zone will be increased. Conversely, the amount of OH doping agent can be lowered, for instance by decreasing the temperature, but without causing a loss of sensitivity of the detector unit 200. The wide range of measurements that can be obtained using the proposed concept is one of the significant advantages over existing detecting devices. The compact and airtight design is another one.

There is also provided in the present concept a method of conducting spectroscopic analyses of gas mixtures. The method includes simultaneous steps. These steps are including:

receiving a stream of carrier gas from a gas chromatograph into a housing, the carrier gas stream containing at least one analyte;
receiving a makeup gas stream into the housing;
mixing the makeup gas stream with an OH doping agent coming from a semi-permeable membrane located at least partially inside a chamber of the housing;
mixing the carrier gas stream with the makeup gas stream inside the housing to form a mixed gas stream;
creating a plasma emission with the mixed gas stream inside the housing;
measuring a light radiation resulting from the plasma;
channeling the mixed gas stream out of the housing; and
controlling the OH doping agent by monitoring and adjusting the temperature of the chamber in the housing in which the semi-permeable membrane is located.

Optionally, the step of measuring the light radiation from the plasma includes sensing the light radiation passing through a transparent wall of the housing. Also, the step of mixing the makeup gas stream with the OH doping agent inside the housing includes heating the housing to control an amount of the OH doping agent coming out of the semi-permeable membrane.

The present detailed description and the appended figures are meant to be exemplary only. A skilled person will recognize that variants can be made in light of a review of the present disclosure without departing from the proposed concept.

LIST OF REFERENCE NUMERALS 100 gas chromatograph
102 sample gas source
104 injector
106 carrier gas source
108 filter
110 carrier gas flow regulator
112 makeup gas flow regulator
114 dryer
116 oven
118 column(s)
120 micro-controller unit
122 computer screen
124 chromatogram
130 discharge power supply
140 carrier gas outlet
142 makeup gas outlet
200 detector unit
210 housing
212 first workpiece
214 second workpiece
216 first cavity
218 second cavity
220 carrier gas inlet
222 carrier gas inlet conduit
224 carrier gas inlet chamber
230 makeup gas inlet
232 makeup gas inlet chamber
234 first passageway
236 second passageway
238 intersection zone
240 ionization chamber
242 third passageway
244 outlet chamber
250 gas outlet
252 outlet conduit
260 light collection window areas
262 light sensors
270 permeation device
272 semi-permeable membrane
274 rigid outer tube
276 makeup gas inlet conduit
280 electric heater element
282 electric heater element
290 first electrode
292 second electrode
300 temperature sensor
400 graph
402 $H_2$ peak
404 $N_2$ peak
406 $CH_4$ peak
408 CO peak
500 graph
502 $H_2$ peak
504 $N_2$ peak
506 $CH_4$ peak
508 CO peak
600 graph
602 $H_2$ peak
604 $N_2$ peak
606 $CH_4$ peak
608 CO peak

What is claimed is:

1. A micro-plasma emission detector unit for use with a gas chromatograph, the detector unit including:

an airtight housing made of a monolithic block of a transparent material and having an internal ionization chamber, the housing including a carrier gas inlet and a gas outlet that are in fluid communication with the ionization chamber through internal passageways, the housing further including a makeup gas inlet and a makeup gas inlet chamber, the makeup gas inlet chamber being in fluid communication with the carrier gas inlet upstream the ionization chamber, and at least one light collection window area in registry with the ionization chamber;
a pair of spaced-apart ionization electrodes provided in the housing and positioned on opposite sides of the ionization chamber; and
a permeation device containing a semi-permeable membrane, the semi-permeable membrane being at least partially and removably insertable inside the makeup gas inlet chamber.

2. The detector unit as defined in claim 1, further including at least one electric heater element attached on the housing.

3. The detector unit as defined in claim 2, wherein the at least one electric heater element includes a metal layer attached to a corresponding outer surface of the housing.

4. The detector unit as defined in claim 3, wherein the at least one electric heater element is made using a film formed by metal deposition.

5. The detector unit as defined in claim 4, wherein the film is made of material selected from the group consisting of silver, aluminum, copper, brass and alloys thereof.

6. The detector unit as defined in claim 3, wherein the at least one electric heater element is attached to the housing using epoxy.

7. The detector unit as defined in claim 1, wherein the monolithic block includes two workpieces made integral to one another.

8. The detector unit as defined in claim 7, wherein the two workpieces are fused together at corresponding major side faces.

9. The detector unit as defined in claim 8, wherein one of the two workpieces is larger in height than the other, the makeup gas inlet chamber being provided on a side of the larger one of the two workpieces.

10. The detector unit as defined in claim 9, wherein the ionization chamber is provided between the corresponding major side faces of the two workpieces.

11. The detector unit as defined in claim 10, wherein the ionization chamber is formed by a cavity machined into the major side face of the smaller one of the two workpieces, the ionization chamber being closed by the major side face of the larger one of the two workpieces.

12. The detector unit as defined in claim 8, wherein the housing is made of material selected from the group consisting of quartz, borosilicate, industrial grade sapphire and synthetic diamond.

13. The detector unit as defined in claim 12, wherein the housing is generally rectangular.

14. The detector unit as defined in claim 1, wherein the electrodes are positioned in opposite corresponding cavities on the housing.

15. The detector unit as defined in claim 1, further including at least one light sensor positioned in registry with the at least one light collection window area.

16. The detector unit as defined in claim 1, further including a temperature sensor provided in the housing adjacent to the makeup gas inlet chamber.

* * * * *